United States Patent
Vargo

(10) Patent No.: US 12,029,396 B2
(45) Date of Patent: Jul. 9, 2024

(54) LARYNGOSCOPE

(71) Applicant: Bradley J. Vargo, Kirtland, OH (US)

(72) Inventor: Bradley J. Vargo, Kirtland, OH (US)

(73) Assignee: Bradley J. Vargo, Kirtland, OH (US)

(*) Notice: Subject to any disclaimer, the term of this patent is extended or adjusted under 35 U.S.C. 154(b) by 987 days.

(21) Appl. No.: 17/004,475

(22) Filed: Aug. 27, 2020

(65) Prior Publication Data

US 2021/0059512 A1 Mar. 4, 2021

Related U.S. Application Data

(60) Provisional application No. 62/894,175, filed on Aug. 30, 2019.

(51) Int. Cl.
| | | |
|---|---|---|
| *A61B 1/267* | (2006.01) | |
| *A61B 1/00* | (2006.01) | |
| *A61B 1/05* | (2006.01) | |
| *A61B 1/06* | (2006.01) | |
| *A61B 90/90* | (2016.01) | |

(52) U.S. Cl.
CPC .......... *A61B 1/267* (2013.01); *A61B 1/00016* (2013.01); *A61B 1/00027* (2013.01); *A61B 1/00066* (2013.01); *A61B 1/05* (2013.01); *A61B 1/0684* (2013.01); *A61B 90/90* (2016.02)

(58) Field of Classification Search
CPC ... A61B 1/267; A61B 1/2673; A61B 1/00016; A61B 1/00027; A61B 1/00066; A61B 1/05; A61B 1/0052; A61B 1/0684; A61B 90/90
USPC ........................................................ 606/194
See application file for complete search history.

(56) References Cited

U.S. PATENT DOCUMENTS

| | | | |
|---|---|---|---|
| 2,354,471 A | 7/1944 | Macintosh | |
| 2,646,036 A | 7/1953 | Allyn et al. | |
| 4,678,608 A | 7/1987 | Dugliss | |
| 4,717,511 A | 1/1988 | Koroscil | |
| 5,277,173 A | 1/1994 | Cantele | |

(Continued)

FOREIGN PATENT DOCUMENTS

| | | |
|---|---|---|
| WO | WO 03/075979 A2 | 9/2003 |
| WO | WO 2019/032459 A1 | 2/2019 |
| WO | WO 2021/041626 A1 | 3/2021 |

OTHER PUBLICATIONS

International Search Report dated Feb. 8, 2021 for International application No. PCT/US2020/48133.

(Continued)

*Primary Examiner* — Eduardo C Robert
*Assistant Examiner* — Christina Negrellirodriguez
(74) *Attorney, Agent, or Firm* — Lippes Mathias LLP

(57) ABSTRACT

A video laryngoscope has a handle and a blade. A chemiluminescent light source is disposed inside the handle, along with one or more photovoltaic cells which are optically coupled to convert chemiluminescence emitted by the chemiluminescent light source into electrical power. An image sensor is disposed on the blade or in the handle and is configured to image the glottis of a patient when the distal end of the laryngoscope blade operatively engages the tongue of the patient. The image sensor is powered by the electrical power produced by the one or more photovoltaic cells. A system for recording tracheal intubation procedures performed by a plurality of video laryngoscopes is also disclosed.

20 Claims, 3 Drawing Sheets

(56) References Cited

U.S. PATENT DOCUMENTS

| | | | |
|---|---|---|---|
| 9,459,326 | B2 | 10/2016 | McGrath et al. |
| 9,559,553 | B2 | 1/2017 | Bae |
| 2005/0065496 | A1 | 3/2005 | Simon et al. |
| 2009/0209816 | A1* | 8/2009 | Gunther Nielsen ............... A61B 1/00006 600/118 |
| 2011/0301414 | A1 | 12/2011 | Hotto et al. |
| 2014/0160261 | A1 | 6/2014 | Miller et al. |
| 2016/0338581 | A1 | 11/2016 | McGrath |
| 2017/0258311 | A1 | 9/2017 | Merz et al. |
| 2017/0367567 | A1 | 12/2017 | Swift |
| 2018/0168433 | A1 | 6/2018 | Meyer et al. |
| 2019/0205567 | A1* | 7/2019 | Shelton, IV ........ G06F 21/6254 |
| 2019/0229559 | A1 | 7/2019 | Boccoleri et al. |

OTHER PUBLICATIONS

Written Opinion of the International Searching Authority dated Feb. 8, 2021 for International application No. PCT/US2020/48133.
International Search Report dated Sep. 23, 2021 for International application No. PCT/US2021/01620.
Written Opinion of the International Searching Authority dated Sep. 23, 2021 for International application No. PCT/US2021/01620.
Baker, Paul A. et al., "*Visual Acuity During Direct Laryngoscopy at Different Illuminance Levels*" www.anesthesia-analgesia.org, Feb. 2013, vol. 116, No. 2, pp. 343-350.
Tousigant, Guy et al., "*Equipment—Light intensity and area of illumination provided by various laryngoscope blades*" Canadian Journal of Anesthesia, 1994, 41:0, pp. 865-869.
Aslan, Kadir et al., "*Metal-Enhanced Chemiluminescence: Advanced Chemiluminescence Concepts for the $21^{st}$ Century*", Chemical Society Reviews, Jun. 10, 2009, doi: 10.1039/b807498b.
Ray, Krishanu et al., "*Aluminum Nanostructured Films as Substrates for Enhanced Fluorescence in the Ultraviolet-Blue Spectral Region*", Analytical Chemistry, Aug. 8, 2007, doi: 10.1021/ac0713631.
Article titled "*Microbiology with Aquaspark™: A Novel Tool for Enzymatic Activity Detection*", Biosynth Chemistry & Biology / Nemis Technologies, Product Mini Reviews 2018.
Scholz, Anette, et al., "Minimum and optimum light output of Macintosh size 3 laryngoscopy blades: a manikin study" https://doi.org/10.1111/j.1365-2044.2006.04912.x, Jan. 10, 2007.
Sherman, Jodi, "*Reusable vs. Disposable Laryngoscopes*", https://apsf.org/newsletter/february-2019, Feb. 2019.
Storz, Karl, "*C-MAC® S Video Laryngoscope and Laryngobloc Cold Light Laryngoscope*", EndoWorld® AN 13 6.1, Jan. 2018.
Janeway, Henry H., "*Intra-Trachael Anesthesia from the Standpoint of the Nose, Throat and Oral Surgeon with Description of a New Instrument for Catheterizing the Trachea*", From the Department of Experimental Surgery of New York University and Bellevue Hospital Medical College, pp. 1082-1090, Date Unknown.
Datasheet titled "*Schott® Image Conduit*", Date Unknown.

\* cited by examiner

LARYNGOSCOPE

This application claims the benefit of U.S. Provisional Application No. 62/894,175 filed Aug. 30, 2019 and titled "LARYNGOSCOPE". U.S. Provisional Application No. 62/894,175 filed Aug. 30, 2019 and titled "LARYNGOSCOPE" is incorporated herein by reference in its entirety.

BACKGROUND

The following relates to laryngoscopy arts, tracheal intubation arts, and the like.

A laryngoscope is a device used by an anesthesiologist or other medical professional in order to look inside a patient's pharynx to view the larynx, vocal cords, and glottis. A common use of a laryngoscope is during tracheal intubation, where a laryngoscope is used to visually monitor insertion of a tracheal tube to ensure the tube is inserted into the tracheal opening, rather than into the neighboring esophageal opening. A typical commercially available laryngoscope includes a handle on which a straight or curved laryngoscope blade is mounted, with the blade typically oriented roughly perpendicularly to the handle. The laryngoscope blade is inserted into the patient's mouth and is used to move the tongue and epiglottis aside to provide an unimpeded view of the glottis. In a tracheal intubation procedure, this maneuver also provides an unobstructed path for insertion of a tracheal tube into the tracheal opening. A lamp is mounted on the blade (or in the handle, with a light conduit directing the light out and along the blade) and is powered by a battery disposed in the handle in order to provide illumination of the larynx and glottis. Macintosh, U.S. Pat. No. 2,354,471 issued Jul. 25, 1944 discloses a curved blade design commonly known as a Macintosh blade. However, other types of laryngoscope blades such as straight blades (for example, a Miller blade, see, e.g. Swift, U.S. Pub. No. 2017/0367567 A1) are also known and used for various laryngoscopy tasks. A given laryngoscope blade shape may be optimized for anatomical particularities of a particular class of patients, and/or for a particular laryngoscopy procedure. For example, some laryngoscope blades incorporate a tube guide for guiding a tracheal tube.

In a variant approach, laryngoscope designs that replace the battery with a chemiluminescent light source are described in Cantele, U.S. Pat. No. 5,277,173 and Weinmann, Int'l. Pub. WO 2019/032459 A1.

Video laryngoscopes have also been developed, that employ a video camera to image the larynx and tracheal opening. See, e.g. McGrath, U.S. Pub. No. 2016/0338581 A1; Merz et al., U.S. Pub. No. 2017/0258311 A1. Video laryngoscopes have been commercialized, e.g. the GlideScope® line of laryngoscopes available from Verathon Inc. Video laryngoscopes may have a separate video monitor, or may have a video monitor incorporated into the handle, or as some other integral part of the video laryngoscope. Video laryngoscopes utilize either a battery or an external power source, and can be particularly useful for more challenging tracheal intubation procedures.

An issue that can arise in laryngoscope procedures is the potential for unwarranted medical malpractice claims. In some instances, a patient may make a claim against the anesthesiologist alleging that a tracheal intubation procedure caused dental or oral damage. In spite of adequate pre-evaluation, it can be difficult to demonstrate that the damage was a pre-existing condition, or occurred during the medical procedure subsequent to intubation. As the cost of the liability claim is typically relatively low, insurance companies often settle such claims to avoid the cost of litigation. However, this can reflect negatively on the anesthesiologist, and may lead to a rate increase for liability insurance. Hence, it would be desirable to reduce the incidence of filed claims and resulting settlements.

Certain improvements are disclosed herein.

BRIEF SUMMARY

In accordance with some illustrative embodiments disclosed herein, a video laryngoscope comprises: a handle; a laryngoscope blade having a proximal end connected with the handle and a distal end that is distal from the handle; a chemiluminescent light source disposed inside the handle; one or more photovoltaic cells disposed inside the handle and optically coupled with the chemiluminescent light source to convert chemiluminescence emitted by the chemiluminescent light source into electrical power; and an image sensor disposed on the laryngoscope blade or in the handle and configured to image the glottis of an associated patient when the distal end of the laryngoscope blade operatively engages the tongue of the associated patient. The image sensor is powered by the electrical power produced by the one or more photovoltaic cells.

In accordance with some illustrative embodiments disclosed herein, a laryngoscope comprises: a handle; a laryngoscope blade having a proximal end connected with the handle and a distal end that is distal from the handle; an electrical power device disposed inside the handle and configured to emit electrical power; and at least one of a light emitting diode (LED) and/or an image sensor disposed on or in the laryngoscope and arranged to illuminate and/or view the glottis of an associated patient when the laryngoscope blade operatively engages the tongue of the associated patient. The LED and/or image sensor is powered by the electrical power emitted by the electrical power device. The electrical power device comprises a chemiluminescent light source disposed inside the handle, and one or more photovoltaic cells disposed inside the handle and optically coupled with the chemiluminescent light source to convert chemiluminescence emitted by the chemiluminescent light source into the electrical power.

In accordance with some illustrative embodiments disclosed herein, a laryngoscope comprises: a handle; a laryngoscope blade having a proximal end connected with the handle and a distal end that is distal from the handle; an electrical power device disposed inside the handle and configured to emit electrical power; and at least one of a light emitting diode (LED) and/or an image sensor disposed on or in the laryngoscope and arranged to illuminate and/or view the glottis of an associated patient when the laryngoscope blade operatively engages the tongue of the associated patient. The LED and/or image sensor is powered by the electrical power emitted by the electrical power device. The electrical power device comprises an electrical coil disposed inside the handle to emit the electrical power comprising an electrical current induced in the electrical coil.

In accordance with some illustrative embodiments disclosed herein, a system is disclosed for recording tracheal intubation procedures performed by a plurality of video laryngoscopes. The system comprises a server computer and at least one user interface device. The server computer is configured to connect with a video laryngoscope of the plurality of video laryngoscopes and to receive video from the connected video laryngoscope and to process the video by operations including performing face identification on the video and removing any frames of the video depicting a human face to generate anonymized video, tagging the anonymized video with a video recording timestamp and at least one of (i) a surgical location and/or (ii) or an anesthesiologist identifier, and storing the anonymized video with the tags on a non-transitory storage medium. At least one user interface device is configured to retrieve selected anonymized video from the non-transitory storage medium. The selected anonymized video is selected on the basis of the video recording timestamp and the surgical location and/or anesthesiologist identifier.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Figure 1:
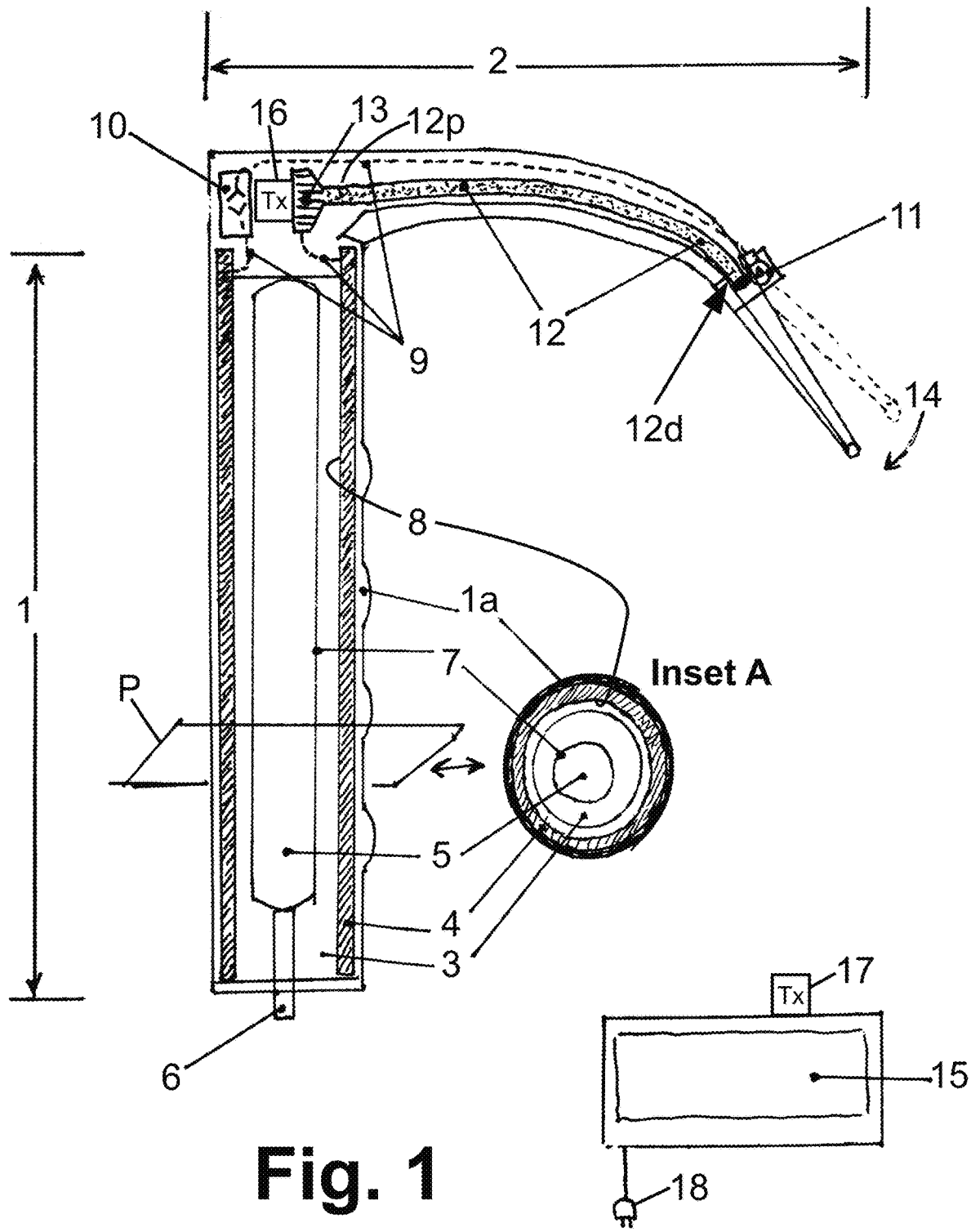
FIG. 1 diagrammatically shows a video laryngoscope including an electrical power supply comprising a chemiluminescent light source coupled with a bank of photovoltaic cells.

Tracheal intubation procedures are very common. For example, in 2010 more than 30 million such procedures were performed in the United States. In most waste disposal jurisdictions (including in the United States), the laryngoscope blade after use must be treated as infectious medical waste, since it mates with a mucous membrane of the patient. The handle, on the other hand, does not come into contact with mucous membranes, and hence may not be considered infectious waste but is a significant vector for contamination of work surfaces between patient care encounters. In some commercial laryngoscope designs, the laryngoscope is a one-piece unit in which the handle is integrally formed with the blade, e.g. as a one-piece molded plastic device. In such designs, the laryngoscope is often a single-use disposable item. In other commercial laryngoscope designs, the blade is detachable from the handle, and may be a durable item (e.g., sterilized by autoclaving between patients). Even in a two-piece design, however, the laryngoscope may still be treated as a single-use disposable item, an advantage being that the handle can be disposed of separately as ordinary waste and thereby reducing the total volume of infectious waste to be processed by the hospital.

In most regulatory jurisdictions, the battery disposed in the handle (to power the lamp) is considered a type of recyclable and/or hazardous waste, although it is not infectious waste. Hence, the battery must be disposed of in accordance with jurisdictional regulations and/or environmentally conscious healthcare system initiatives governing battery disposal, which are different from the regulations governing disposal of infectious waste. This means that after using the laryngoscope, the battery must be removed and disposed of in a regulatory-compliant battery disposal receptacle, separately from the disposal of the laryngoscope in the infectious waste receptacle (and, optionally, the handle in ordinary waste in the case of a separable two-piece design).

While the extra step of disposing of the battery may seem inconsequential, in practice it is troublesome in a surgical setting. The advantages of a single-use disposable laryngoscope include simplicity and the assurance that the battery is fully charged at the start of the laryngoscopy procedure. However, the need to remove the battery along with placing the single-use disposable laryngoscope (or at least its blade) into the infectious waste receptacle means that the surgical operating room must be equipped with a compliant battery disposal receptacle and personnel. Moreover, the battery can lose charge during storage, leading to inadequate illumination and potential intubation failure. Battery powered electric lamps can also be prone to unreliability due to intermittent electrical contacts, which can lead to sudden and complete loss of illumination, potentially during the tracheal intubation process. These issues can introduce delays in the surgical procedure, which is undesirable in many clinical settings in which the surgical operating room is scheduled for a number of surgical sessions in a given day with only short intervals allocated between surgical sessions, and can also lead to undesirable patient outcomes, patient injury or even death.

Laryngoscope designs have been described in which a chemiluminescent light source replaces the battery. However, in this design the optical output power of the chemiluminescent light source would need to be sufficiently high (i.e., sufficiently bright) to provide sufficient illumination for visual observation of the glottis of the patient when the laryngoscope blade operatively engages the tongue of the patient. In one described design (Cantele, U.S. Pat. No. 5,277,173), the chemiluminescent light source is disposed in the laryngoscope blade. While this advantageously places the chemiluminescent light source in close proximity to the distal end of the blade, it requires some modification (and likely enlargement) of the blade in order to accommodate the integration of the chemiluminescent light source into the blade. These considerations may also limit the size of the chemiluminescent light source, which will lower the optical output power. In other designs (Weinmann, Int'l. Pub. WO 2019/032459 A1) the chemiluminescent light source is disposed in the handle and a light conduit is provided to convey the chemiluminescence to the distal end of the blade. This approach may allow for a larger chemiluminescent light source, but the light conduit introduces optical losses, especially at the optical coupling of the light conduit to the chemiluminescent light source.

On the other hand, video laryngoscopes are commercially available. A video laryngoscope contains an on-board camera, and is typically connected with a separate video monitor by a cable. This allows the camera and light source of the video laryngoscope to be powered via the connection cable, which is also used to transmit video from the camera to the separate video monitor. The blade-mounted camera is positioned to directly observe the glottis of the patient when the laryngoscope blade operatively engages the tongue of the patient. However, the camera can complicate design of the blade. Moreover, most tracheal intubation procedures are straightforward, and can be performed by a competent anesthesiologist in less than one minute. For such routine procedures, employing a video laryngoscope can actually slow down the procedure, as the connecting cable must be connected between the video laryngoscope and the monitor, and that cable can physically interfere with the anesthesiologist or other surgical personnel. The cable can also interfere with manipulation of the laryngoscope and can be prone to connection failure after prolonged use.

With reference to FIG. 1, a video laryngoscope is disclosed. The laryngoscope includes a handle 1 and a laryngoscope blade 2. The handle 1 may be integral with, or separate from, the blade 2. The laryngoscope blade 2 connects with the handle 1 at a proximal end of the blade 2, while a distal end 14 of the blade 2 is sized and shaped to operatively engage the tongue of a patient to assist an anesthesiologist in performing a tracheal intubation (or, more generally, to facilitate viewing the glottis of the patient by way of the distal end 14 of the laryngoscope blade 2 operatively engaging the tongue of the patient to move it out of the way).

The handle 1 is hollow, having an exterior wall 1a made of, for example, hard polycarbonate/acrylic (although other materials, including metal, are contemplated for the exterior wall 1a). The handle 1 is shown in sectional view in FIG. 1 (as well as in the other drawings herein). Furthermore, Inset A shows a cross-sectional view of the handle 1 at the indicated cross-section plane P. A chemiluminescent light source is provided inside the hollow handle 1. The chemiluminescent light source includes a first reactant fluid 3 disposed in a first container 8, and a second reactant fluid 5 disposed in a second container 7, which is fragile as will be described. Upon rupture of the fragile second container 7, for example by action of a plunger 6 that fractures the second container 7, the first and second reactant fluids 3, 5 combine and produce chemiluminescence. Optionally the mixing of the reactant fluids 3, 5 may be improved by shaking the laryngoscope after activating the plunger 6.

A bank of photovoltaic cells 4 are arranged around the periphery of the first container 8, which is optically transparent to the chemiluminescence. The photovoltaic cells 4 convert chemiluminescence generated by the reaction of the first and second reactant fluids 3, 5 into electrical power. Electrical wiring (or more generally, electrical conductors) 9 electrically connect the photovoltaic cells 4 to a power/voltage modulator/regulator (or, more generally, one or more power conditioning electrical components) 10 which condition the electrical power supplied by the photovoltaic cells 4 to power a light emitting diode (LED) 11 that is arranged on (or in) the blade 2 to illuminate the glottis of the patient when the distal end of the laryngoscope blade 2 operatively engages the tongue of the patient.

Additionally, the video laryngoscope of FIG. 1 includes an image sensor 13 disposed on the laryngoscope blade 2 or in the handle 1. As the image sensor 13 is typically used in acquiring video, a term such as "video sensor" may also be used herein to refer to the image sensor 13. (However, it is contemplated to also acquire one, two, or more still images using the sensor 13 for purposes such as documenting the intubation procedure). The image sensor 13 is powered by electrical power from the photovoltaic cells 4 delivered via the wiring 9. In one embodiment, the image sensor 13 is a CMOS image sensor, although an imaging sensor employing another imaging technology is contemplated. The image sensor 13 is configured to image the glottis of the patient when the distal end of the laryngoscope blade 2 operatively engages the tongue of the patient. The LED 11 provides the illumination light for this imaging. As seen in FIG. 1, the illustrative image sensor 13 is disposed at the proximal end of the blade 2. This does not provide the image sensor 13 with a direct view of the glottis. To address this, an image conduit 12 is provided. The image conduit 12 has a first (i.e. distal) end 12d disposed on the laryngoscope to view the glottis of the patient when the distal end 14 of the laryngoscope blade 2 operatively engages the tongue of the patient. The image conduit extends along at least a portion of the laryngoscope blade 2 and terminates at a second (i.e. proximal) end 12p that is operatively connected with the image sensor 13. The image conduit 12 is a rigid fiber optic rod, e.g. a fused optical fiber, that is designed to transmit a coherent image. Preferably, the rigid image conduit 12 is heated in order to be bent to conform with the curvature of the blade 2; after cooling, the conformally bent image conduit 12 regains its rigidity. It will be appreciated that an advantage of employing the image conduit 12 is that the image sensor 13 can thereby obtain high quality images of the glottis without requiring the image sensor 13 to be disposed closer to the distal end 14 of the blade 2 to directly view the glottis. This reduces or eliminates the need to modify the blade 2 to accommodate the image sensor 13, and allows for placement of the image sensor 13 at the proximal end of the blade 2 where there is more space to accommodate the image sensor 13. Furthermore, this proximal placement of the image sensor 13 reduces the length of the portion of the wiring 9 that connects the image sensor 13 to the photovoltaic cells 4. (It is contemplated to alternatively dispose the image sensor in the handle 1 near the proximal end of the blade, in which case the image conduit 12 would be bent in an arc to connect with the image sensor in the handle).

The image sensor 13 includes, or is operatively connected with, a radio transmitter 16 that wirelessly transmits images acquired by the image sensor 13 to a separate video monitor 15 (via a corresponding radio receiver 17 of the video monitor 15). Typically, the on-board radio transmitter 16 and the corresponding radio receiver 17 of the video monitor 15 are both transceivers, so as to allow pairing (i.e., defining of a dedicated wireless communication channel) of the laryngoscope and the video monitor 15. In a suitable embodiment, both transceivers 16, 17 are Bluetooth transceivers and employ conventional Bluetooth wireless transmission protocols. For example, by way of non-limiting illustration, transceivers employing Bluetooth Low Energy, i.e. Bluetooth LE or BLE, are particularly well suited for the transceivers 16, 17 due to the low power draw of BLE. The illustrative on-board radio transceiver 16 is operatively connected with the image sensor 13 so that it receives power from the photovoltaic cells 4 together with the image sensor 13. Alternatively, the radio transceiver 16 may be a separate component operatively connected with the image sensor, in which case additional wiring 9 is suitably provided to power the radio transceiver 16 using the photovoltaic cells 4. The on-board radio transceiver 16 may, by way of non-limiting illustration, comprise a microprocessor or IC with low power draw, such as an Advanced RISC Machine, i.e. ARM, processor. The separate video monitor 15 may be powered by an electrical plug 18, as shown, or by an on-board electrical battery. In a variant embodiment (not shown), it is contemplated to replace the separate video monitor 15 by an on-board video monitor that is mounted to the handle 1 or to the proximal portion of the blade 2, i.e. on the blade near its connection with the handle 1. In this variant embodiment, the on-board video monitor would be suitably powered by the photovoltaic cells 4. In some embodiments, the on-board video monitor would connect with the handle or proximal portion of the blade of the laryngoscope via a detachable connection, so that the on-board video monitor could be removed and reused.

In general, the video acquisition process involves acquiring successive images (i.e. frames) at a chosen frame rate, e.g. at 30 frame/second (i.e. 30 fps) in televised video although the video laryngoscope can operate at a different fps if desired. Each frame is acquired by the image sensor 13 and the image data making up the frame is transmitted from the image sensor 13 to the video monitor 15 via the paired transceivers 16, 17. The electronic processing involved in the video acquisition can be variously divided between on-board electronics of the image sensor 13 disposed in the laryngoscope and electronics of the video monitor 15. In one approach, the electronic processing is mostly performed at the video monitor 15, e.g. the video monitor sends trigger signals to the image sensor at the frame rate, and in response to reach received trigger signal the image sensor acquires a single image and sends it back to the video monitor which receives the images and constructs and displays the video stream. This approach advantageously reduces the electronic data processing power overhead of the image sensor 13, but may require the video monitor 15 to be a dedicated monitor designed specifically to operate with the laryngoscope. In other embodiments, the electronic processing is performed mostly by on-board electronics of the image sensor 13 disposed in the laryngoscope. In this approach, the on-board electronics of the image sensor 13 automatically acquire frames at the frame rate, converts the frames to a video stream in a video format (e.g. AVI, FLV, WMV, MOV, MP4, . . . ) and transmits the video stream to the video monitor. This approach entails higher processing power overhead at the image sensor 13, but makes the video laryngoscope compatible with standard video monitors that can receive a wireless video stream via Bluetooth or another wireless communication protocol.

In a suitable implementation of the laryngoscope of FIG. 1, the blade 2 has a design in the Macintosh style, but has an exaggerated curve at the distal ⅓ portion 14. This exaggerated curve permits the low power consumption LED 11 and an optional lens to be mounted in a manner that can improve the visual axis of observing the glottis during video laryngoscopy. The handle 1 contains two compartments 7, 8 housing to separate chemical reactant fluids 3, 5 separated by the breakable inner container 7 (containing the second reactant fluid 5) with the plunger 6 that fractures the inner container 7 when pressed. The internal aspect of the outer most portion of the hollow laryngoscope handle 1 is lined with the photovoltaic cells 4. As chemiluminescence is produced, electrical current begins to power the CMOS image sensor 13 and the Bluetooth transmitter 16 mounted at the proximal (base, close to the handle) portion of the blade 2. The electrical power generated by the photovoltaic cells 4 also powers the LED 11 (the same bank of cells powers both, or alternatively separate banks of photovoltaic cells are provided for powering the image sensor 13 and LED 11, respectively). The illustrative voltage regulator or modulator 10 connects to the LED by the electrical wiring or the like. The Bluetooth (or other wireless communication) capabilities send wireless video data to the nearby durable high definition video screen and/or video processor 15. Note that the video monitor 15 is not shown to the same scale as the laryngoscope in FIG. 1.

The chemiluminescent light source is particularly well suited for use as the illumination source in a laryngoscope. A chemiluminescent light source is a single-use light source, which comports with its use in a single-use disposable laryngoscope. Furthermore, the chemiluminescent light source is typically not considered hazardous waste, as the chemicals employed can be chosen to be noncorrosive and non-toxic. As such, a single-use disposable laryngoscope employing a chemiluminescent light source can be disposed of as a unit in the infectious waste receptacle, without needing to remove the chemiluminescent light source before disposal. The chemiluminescent light source also maintains the simplicity of use of a single-use disposable laryngoscope. The chemiluminescent light source may be activated using the illustrative plunger 6, or by another activation mechanism such as squeezing the handle of the laryngoscope, or giving the laryngoscope a vigorous shake before use, depending upon the design.

There is a design tradeoff in designing the operating characteristics of the chemiluminescent light source. It is possible to design a chemiluminescent light source for higher intensity, at the cost of shorter operational lifetime, by suitable selection of the chemiluminescent fluids and the relative concentrations of the constituents of the chemiluminescent fluids. Hence, the chemiluminescent light source can optionally be optimized for a shorter operating lifetime of a few minutes or a few tens of minutes, thus allowing for designing it to provide higher intensity light output. However, this approach has limitations that will cancel out the advantages of relatively low cost, low heat and ease of disposability.

However, in the video laryngoscope of FIG. 1, the chemiluminescent light source effectively has its optical power increased by way of using the chemiluminescent light source to power the LED 11. As the photovoltaic cells 4 can surround most (or possibly all) of the exterior surface area of the first (outer) container 8, this means that most (or all) of the emitted chemiluminescent light impinges on the photovoltaic cells 4 and is therefore converted to electrical power with the conversion efficiency of the photovoltaic cells 4. Even with low cost crystalline silicon or thin-film photovoltaic cells, conversion efficiencies of 20% or higher are achievable, meaning that much of the power generated by the chemiluminescent light source is delivered to power the LED 11 and the image sensor 13 and radio transceiver 16. By contrast, laryngoscope designs to use a chemiluminescent light source to provide direct illumination of the glottis (by the chemiluminescence itself) may suffer substantial optical losses at the optical coupling between the chemiluminescent light source and the light conduit. Even in designs in which the chemiluminescent light source is disposed in the blade itself, optical losses can be high since most of the generated chemiluminescence is not directed toward the glottis.

As yet a further advantage, the nature of the chemiluminescent light source (a chemical reaction having a fixed reaction rate at atmospheric pressure and typical operating room temperature) ensures that the chemiluminescent light source will stay on for the design-basis operational lifetime. By contrast, a battery can lose charge over time when in storage, so that it may be insufficiently charged at the time of use, or can experience intermittent electrical contact failure during use.

Figure 2:
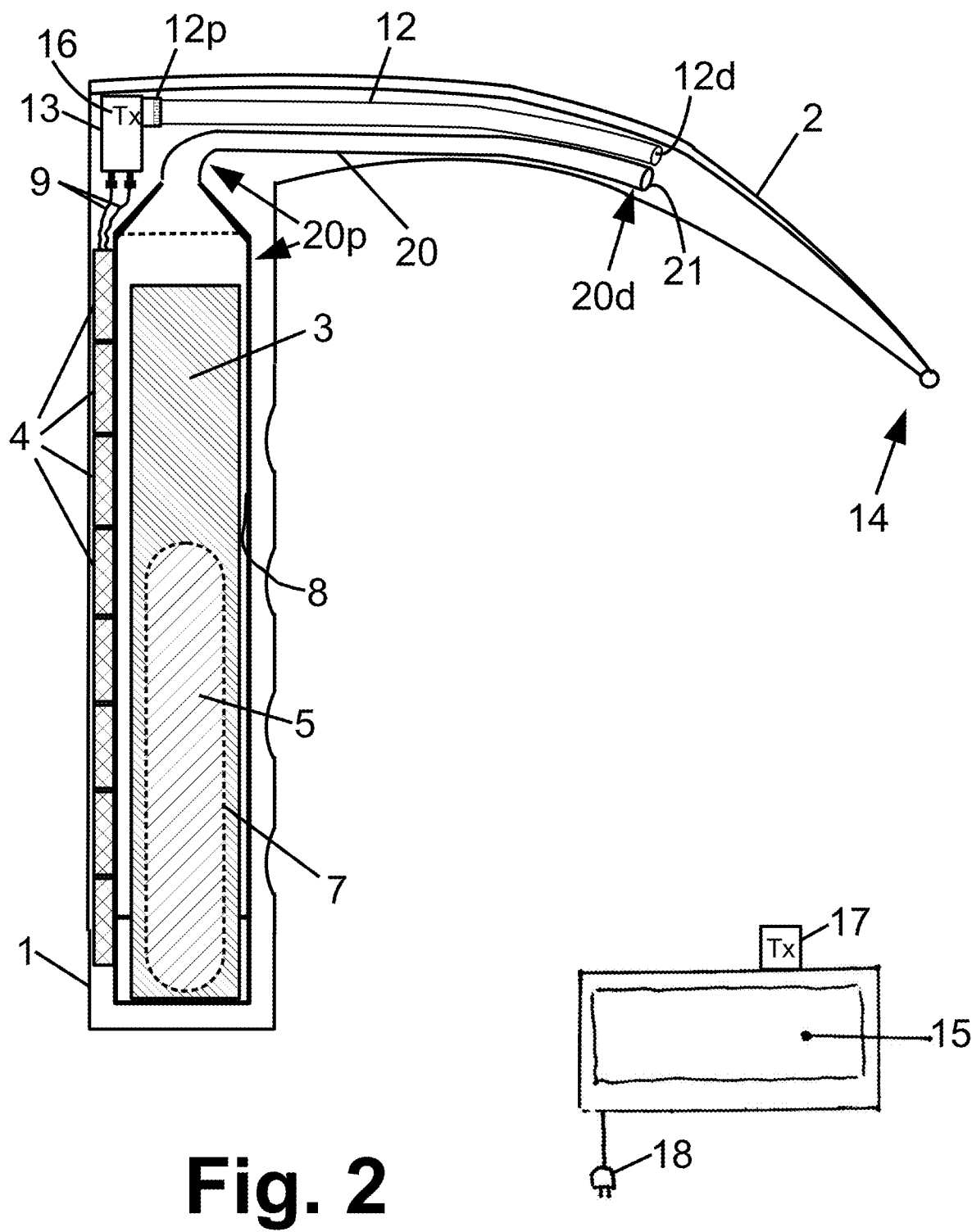
FIG. 2 diagrammatically shows a video laryngoscope including an electrical power supply comprising a chemiluminescent light source coupled with a bank of photovoltaic cells, in which the chemiluminescent light directly illuminates the procedure.

With reference to FIG. 2, another video laryngoscope is shown, which is similar to the laryngoscope of FIG. 1, and includes the handle 1, blade 2 with distal end 14, first and second reactant fluids 3, 5 in respective first and second containers 8, 7, and photovoltaic cells 4 optically coupled with the first container 8. (In FIG. 2, the photovoltaic cells 4 are shown on only one side of the first container 8, but can optionally fully surround the first container 8 as shown in more detail in FIG. 1 including Inset A). The laryngoscope of FIG. 2 further includes the electrical wiring 9, and the image sensor 13 with (here integral) radio transmitter 16 and optically coupled image conduit 12 as already described with reference to FIG. 1. The radio transmitter 16 communicates with the paired video monitor 15 via its transceiver 17, as previously described. The principal difference of the embodiment of FIG. 2 compared with that of FIG. 1 is that the LED 11 and associated power conditioning 10 of FIG. 1 is replaced by direct illumination by the chemiluminescence in the embodiment of FIG. 2. To this end, a light conduit 20 has a proximal end 20p that is optically coupled with the chemiluminescent light source, and the light conduit 20 extends along a portion of the laryngoscope blade 2 and terminates at a distal end 20d. In some embodiments, the light conduit 20 may provide sufficient collimation of the light to form the chemiluminescence into a light beam suitable for illuminating the patient's glottis when the blade 2 is operatively engaged. In other embodiments, at least one optical component 21, such as an illustrative lens 21, is optically coupled with the second, i.e. distal end 20d of the light conduit 20 in order to form light exiting from the second end 64 of the light conduit into illumination for illuminating the patient's glottis. The lens 21 may be a simple lens, or may be a compound lens, Fresnel lens, collimating reflector, or other optical component or combination of optical components suitable for forming the beam. In some embodiments, the optical component 21 may be integrally formed with the distal end 20d of the light conduit 20, for example by heating the distal end 20d of the light conduit 20 (assumed here to be a heat-formable plastic) to cause it to ball up and form a simple lens.

As previously noted, using the chemiluminescence to directly illuminate the glottis can be problematic due to poor light coupling of the chemiluminescent light source into the light conduit. In the embodiment of FIG. 2, this is addressed by forming (the proximal end 20p of) the light conduit 20 to extend into the handle 1, and embedding the chemiluminescent light source in the portion of the light conduit 20 extending into the handle 1. This maximizes the light coupling.

Furthermore, in the embodiment of FIG. 2 it is not necessary for the chemiluminescence to illuminate the glottis well enough for the anesthesiologist to observe the glottis. Rather, it merely must be sufficient to obtain video of the glottis using the image sensor 13. As the image sensor can have much higher light sensitivity than the human eye, the optical power requirements are thereby reduced. Hence, in some embodiments, the optical output power of the chemiluminescent light source is not effective to provide illumination via the light conduit 20 for visual observation of the glottis of the patient when the laryngoscope blade 2 operatively engages the tongue of the patient; but, the optical output power of the chemiluminescent light source is effective to provide illumination via the light conduit 20 for observation of the glottis of the patient via the image sensor 13 when the laryngoscope blade 2 operatively engages the tongue of the patient.

(Similarly, in FIG. 1, the LED 11 need only be bright enough to provide illumination for the image sensor 13 to observe the glottis. Hence, in some embodiments the optical output power of the LED 11 is not effective to provide illumination for visual observation of the glottis of the patient when the laryngoscope blade 2 operatively engages the tongue of the patient; but, the optical output power of the LED 11 is effective to provide illumination for observation of the glottis of the patient via the image sensor 13 when the laryngoscope blade 2 operatively engages the tongue of the patient.)

To further illustrate, the minimum laryngoscope illumination standard for visual observation of the glottis of the patient has been set at 500 lux by the ISO 7376:2009 standard. This value considered to be the minimal optimum illumination level for direct laryngoscopy and tracheal intubation. However, the ISO 7376:2009 standard does not consider individualized preferences, skill levels, experience and conditions, and applies for direct visual observation of the glottis by the anesthesiologist. A study investigating visual acuity at 50 lux, 200 lux, 700 lux, and 2000 lux found that visual acuity is lower at 50 lux than at 200 lux, continues to improve at 700 lux, with no further improvement observed at 2000 lux. See Baker et al., "Visual Acuity During Direct Laryngoscopy at Different Illuminance Levels", Anesthesia-Analgesia vol. 116 no. 2, pp. 343-350 (February 2013). This study also found that the average observation distance for direct laryngoscopy is 32 cm.

Currently available chemiluminescent light sources are unable to provide illumination of 500 lux as required by current ISO standards for direct laryngoscopy. To the contrary, the illuminance produced by a chemiluminescent light source at a distance of 32 cm (the average observation distance for direct laryngoscopy), is expected to be less than 10 lux. Thus, it is recognized herein that employing a chemiluminescent light source as the illumination source in a laryngoscope is expected to be feasible only if the chemiluminescent light source is used in combination with the image sensor 13, e.g. in a video laryngoscope.

Advantageously, an illumination of 200 lux or less, or even 50 lux or less, at a video sensor distance of 2-3 cm is expected to be sufficient for video laryngoscope operation due to the higher sensitivity of the image sensor 13 compared with the acuity of direct visual observation, and the closer placement of the image sensor 13 (e.g. 2-3 cm) during video laryngoscopy compared with the larger distance of the human eye (e.g., 32 cm) during direct laryngoscopy. Laryngoscope embodiments disclosed herein achieve this by a synergistic combination that uses a sensitive, photoelectric powered video sensor and low level illumination (e.g., 200 lux or less at an image sensor distance of 2-3 cm, or in some embodiments 50 lux or less at an image sensor distance of 2-3 cm. This low level illumination is provided directly by the chemiluminescent light source (e.g. FIG. 2) or indirectly by an LED photoelectrically powered by the chemiluminescent light source (e.g. FIG. 1). Thus, laryngoscope embodiments disclosed herein are highly effective, disposable and convenient for use in tracheal intubation for routine anesthesia and all procedures requiring tracheal intubation.

As another variant (not shown) of the embodiment of FIG. 1, it is contemplated to provide a laryngoscope substantially similar to that of FIG. 1, but omitting the image conduit 12, image sensor 13, separate video monitor 15, and associated radio transceivers 16, 17. This embodiment is then not a video laryngoscope. As already discussed with reference to FIG. 1, employing the LED 11 powered by the power device comprising the chemiluminescent light source and coupled photovoltaic cells 4 has substantial advantages over attempting to provide human-visible illumination of the glottis using direct chemiluminescence as the illumination. The chemiluminescent light source effectively has its optical power increased by capturing more of the chemiluminescence via the (mostly or completely) surrounding bank of photovoltaic cells 4. Furthermore, the LED 11 can be designed to output white light whose color spectrum is optimized for visual observation of the glottis, e.g. having desired spectral characteristics (color rendering index, CRI, et cetera). In some embodiments, the LED 11 is contemplated to be designed to illuminate the glottis with both visible light and ultraviolet light, e.g. in the ultraviolet range of 300-450 nm. While the human eye is relatively insensitive to this deep-bluish to ultraviolet range, the ultraviolet light component can stimulate phosphorescence of the vocal cords, thereby increasing their visibility. (This emission of ultraviolet light is also contemplated to be employed in conjunction with the image sensor 13, which may optionally be tuned to detect in the ultraviolet).

In any of the foregoing embodiments, the laryngoscope blade 2 is connected with the handle 1 to form the laryngoscope. In a two-piece laryngoscope design the blade is detachable from the handle, in which case the laryngoscope blade 2 is connectable with the handle 1 to form the laryngoscope. In a one-piece design the laryngoscope blade 2 and the handle 1 are integrally formed. The laryngoscope blade 2 is specially configured for use in a laryngoscopy procedure, and may for example be a curved Macintosh laryngoscope blade (as shown) or a straight (or straighter) Miller laryngoscope blade, although more generally any laryngoscope blade design suitable for clinical use may be employed. It is also contemplated for the laryngoscope blade to include a tube guide (not shown) for guiding a tracheal tube, or other features known in the laryngoscopy arts to be of clinical benefit for specific medical procedures. The handle 1 is sized and shaped for the anesthesiologist (or other user) to hold, and the blade 2 is connected with (or connectable with) the handle 1 in an orientation that facilitates its use in facilitating looking inside the patient's pharynx to view the larynx, vocal cords, and glottis, and in one common application for its use in performing the maneuver in which the laryngoscope blade 2 is inserted into a patient's mouth, and is used to move the tongue and epiglottis aside to provide an unimpeded view of the patient's glottis so as to enable insertion of a tracheal tube. The illustrative laryngoscope blade 2 is mounted with the blade 2 oriented perpendicular to the handle 1, although as seen in FIG. 1 the illustrative curved Macintosh blade 2 is seen to progressively curve further away from perpendicularity with increasing distance away from the handle 1.

The illustrative laryngoscope employs the plunger 6 to activate the chemiluminescent light source. However, other activation mechanisms are contemplated, such as spring-loading the plunger 6 which may provide a more reliable activation of the chemiluminescent light source. In another contemplated approach, a protrusion (not shown) extends inward from the inside wall 1a of the handle, so that squeezing the handle causes the protrusion to rupture the fragile second container 7. In another contemplated approach, a weight (not shown) is disposed in the first container 8, or the second container 7 is movable within the first container 8, so that shaking the laryngoscope causes the fragile second container 7 to rupture due to impact of the weight or impact of the second container directly onto the first container. As yet another contemplated approach, a twist-type or bending-type activation mechanism could be employed, such as is commonly used in chemiluminescent glow sticks such as are used in children's toys and single-use light beacons of the type used in nighttime traffic management. In designing the activation mechanism consideration should be given to the need for the handle 1 to be sufficiently rigid to serve its primary purpose as the hand-hold via which the anesthesiologist manipulates the laryngoscope blade 2 to move the tongue and epiglottis aside in order to provide an unimpeded view of the patient's larynx and tracheal opening and enable insertion of a tracheal tube.

The first reactant fluid 3 and the second reactant fluid 5 can be any suitable combination of reactants that, when reacted together, generate chemiluminescence suitable for illuminating the glottis during a laryngoscopy procedure. In one suitable formulation the first reactant fluid (or, alternatively, the second reactant fluid) comprises hydrogen peroxide, and at least one of the first reactant fluid or the second reactant fluid comprises one or more fluorophores. The first container 8 optionally further includes at least one additional fluorophore disposed on an inner wall of the first container 8. A fluorophore is the chemical group or structural domain of the fluid that is responsible for the fluorescent light output when the two reactant fluids are mixed. (Note, the terms "fluorophore" and "dye" are used interchangeably herein to designate the chemical constituent or constituents that emit light in the chemiluminescence reaction). In one specific example, the first reactant fluid comprises hydrogen peroxide and the second reactant fluid comprises diphenyl oxalate and one or more fluorophores. Reaction of the hydrogen peroxide and diphenyl oxalate upon rupture of the second container generates an intermediate reactant which reacts with and excites the dye molecules to generate the chemiluminescence. The reaction rate is pH-dependent, and a weak base is optionally added to the second reactant fluid to speed up the reaction and increase the light intensity (albeit at the cost of a shorter duration of illumination, but this is acceptable since most tracheal intubation procedures only take a few minutes or less). In one embodiment, the fluorophore(s) output white light. This can be achieved by having multiple fluorophores, e.g. having peak emission at different wavelengths spanning the visible wavelength range. For example, the fluorophore 9,10-Bis(phenylethynyl)anthracene (BPEA) emits at a peak wavelength of 486 nm, the fluorophore rubrene emits orange-yellow at 550 nm, and the fluorophore violanthrone emits orange light at 630 nm, so that a suitable combination of these dyes produces white light. Some other suitable white chemiluminescent light sources are described in Dugliss, U.S. Pat. No. 4,678,608 and Koroscil, U.S. Pat. No. 4,717,511, both of which are incorporated herein by reference in their entireties. Light intensity enhancement may also be obtained by the addition of metallic nanoparticles to one or both fluids. See Ray et al., "Aluminum Nanostructured Films as Substrates for Enhanced Fluorescence in the Ultraviolet-Blue Spectral Region", Anal Chem vol. 79 no. 17, pp. 6480-87 (2007); Asian et al., "Metal-Enhanced Chemiluminescence: Advanced Chemiluminescence Concepts for the $21^{st}$ Century", Chem Soc Rev. vol. 38 no. 9, pp. 2556-64 (2009). These are merely non-limiting illustrative examples, and it is contemplated to employ any suitable fluorophore(s), including proprietary fluorophores, and optional additives.

In the example of FIG. 1, the chemiluminescence does not directly provide human-viewable illumination of the glottis. Consequently, the first and second reactant fluids 3, 5 can be designed to output light whose spectrum optimally couples with the photovoltaic cells 4. This provides much greater flexibility to design the chemiluminescent light source for high optical output power, as compared with laryngoscope designs to employ chemiluminescence to provide human-viewable illumination of the glottis. In the case of FIG. 2, the chemiluminescence does directly provide the illumination—but that illumination is "observed" by the image sensor 13, rather than being viewed by a human. As such, the spectrum of the chemiluminescence can again be designed to optimally match sensitivity of the image sensor 13.

The LED 11 in the embodiment of FIG. 1 may, for example, be a blue- or ultraviolet-emitting gallium nitride (GaN)-based photodiode coated with a white phosphor, or coated with a yellow phosphor of a thickness effective to allow a portion of blue direct GaN emission through so as to form white light. In some embodiments, the direct GaN emission includes an ultraviolet spectral component in the range of 350-450 nm, some of which passes through the phosphor layer to stimulate phosphorescence of the vocal cords, thereby increasing their visibility. However, since the LED light is viewed by the image sensor 13, rather than by a human, the spectrum of light output by the LED can be designed to optimally match sensitivity of the image sensor 13.

The embodiments of FIGS. 1 and 2 use the chemiluminescent light source to generate electrical power to drive the image sensor 13 and (in the embodiment of FIG. 1) the LED 11. However, other electrical power devices are contemplated. For example, the electrical power device may be a near field magnetic induction device. In this approach (not shown), an electrical coil is disposed inside the handle, and electrical conductors connect to the electrical coil to power the image sensor 13 and the LED 11 of FIG. 1. To induce the electric current in the electrical coil, a radio frequency (RF) power generator is provided, which is separate from the handle 1 and separate from the laryngoscope blade 2. The RF power generator generates RF power that inductively couples with the coil thereby inducing the electrical current in the electrical coil by near-field magnetic induction. To limit radio frequency interference, it is desirable for the RF power generator to have low RF power output. To this end, the RF power generator may be located close to the handle, e.g. as a compact unit disposed underneath the head or neck of the patient.

In general, the laryngoscope may be either a one-piece laryngoscope in which the blade 2 and handle 1 are integrally formed; or may be a two-piece laryngoscope in which the blade 2 is detachable from the handle 1. In a two-piece design, the wiring 9 suitably includes electrical connectors that mate together when the handle and blade are connected, and (in the embodiment of FIG. 2), the proximal end 20p of the light conduit 20 includes a suitable optical coupling that mates when the handle and blade are connected together. While the blade 2 may be a disposable or reusable design, the handle 1 of a two-piece design with the chemiluminescent light source may (depending on jurisdictional regulations) be fully disposable and considered non-infectious and non-hazardous waste. In general, the blade 2 may be made of a metal such as stainless steel, or a hard plastic such as polycarbonate or acrylic. Similarly, the handle 1 may be made of a metal such as stainless steel, or a hard plastic such as polycarbonate or acrylic.

Figure 3:
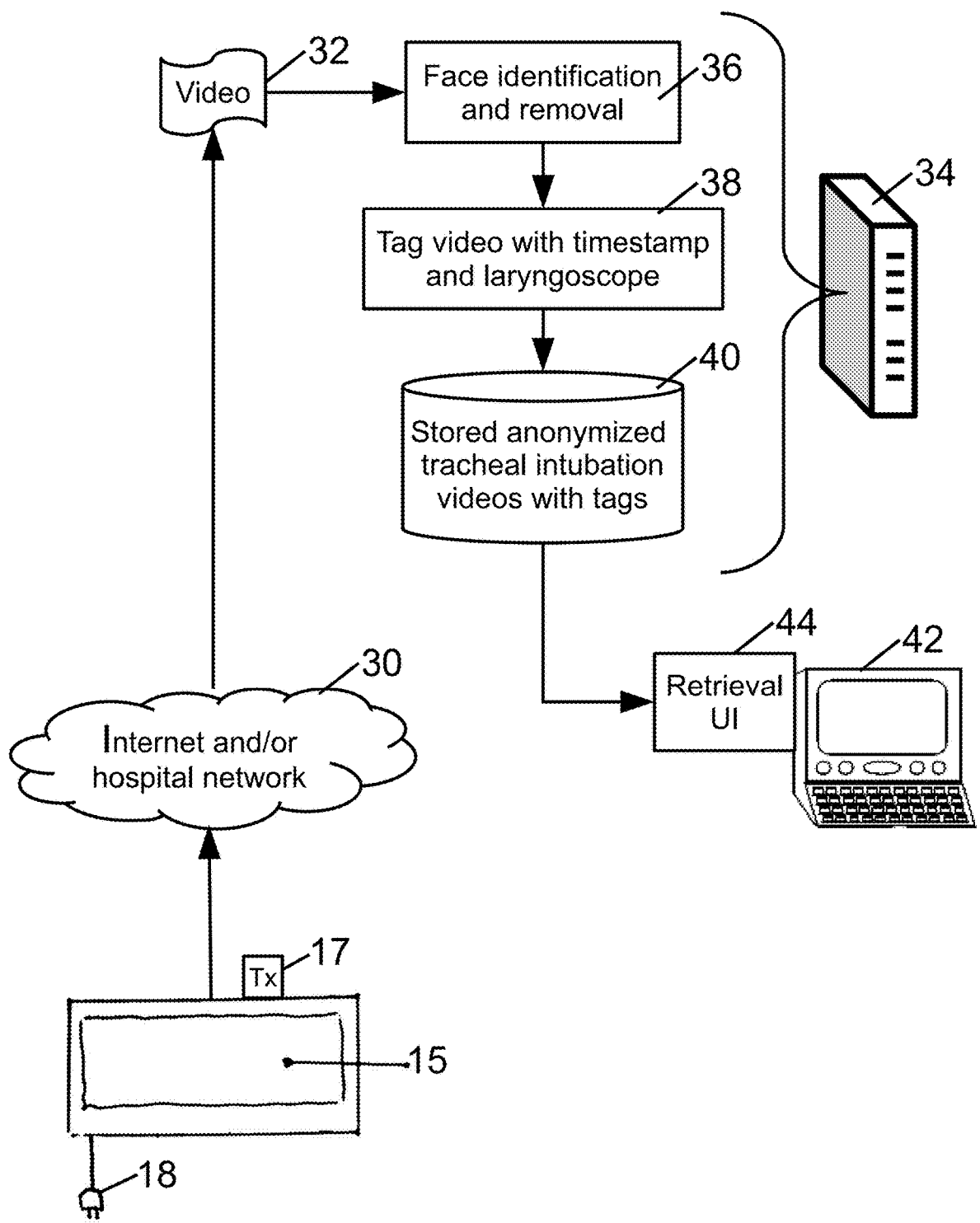
FIG. 3 diagrammatically shows a system for providing anonymized, auditable record of tracheal intubation procedures.

With reference now to FIG. 3, a system is disclosed which leverages a video laryngoscope to provide an auditable record of tracheal intubation procedures. As previously noted, in present practice an anesthesiologist typically has no evidentiary basis for defending against a dental- or vocal cord-related medical malpractice claim. Typically, video laryngoscopes do not record the acquired video, but merely display it on the video monitor. As a tracheal intubation is generally considered a routine procedure, no recordation is usually performed. The disclosed approach leverages the video laryngoscope to automatically record an anonymized record of each performed tracheal intubation. As already described with reference to FIGS. 1 and 2, the video monitor 15 receives and displays video acquired by the video laryngoscope. As further shown in FIG. 3, the video monitor 15 also has connectivity with the Internet and/or a hospital network (e.g. wired and/or wireless Ethernet, WiFi, and/or so forth) 30 and thereby sends the video 32 to a server computer 34. The server computer 34 thus connects with the video laryngoscope (here indirectly via the intermediary of the video monitor 15) to receive the video 32 from the connected video laryngoscope. The server computer 34 is programmed to perform an operation 36 in which face identification is performed on the video 32 and any frames of the video depicting a human face are removed to generate anonymized video. In the operation 36, the face identification merely identifies that a face is depicted in a frame—it does not then proceed to match that face with a particular person whose face is stored in a database, as in conventional facial recognition. Hence, the face identification 36 can employ any algorithm conventionally used in the first phase of facial recognition (the phase of identifying a face is present, e.g. by identifying landmarks such as eyes, nose, and mouth features). The reason for the operation 36 is that, as soon as the chemiluminescent light source is activated video starts to be recorded. Therefore, it is likely that the patient's face will be imaged as the video laryngoscope is moved toward the patient's mouth. Storing such images could constitute a violation of Health Insurance Portability and Accountability Act (HIPAA) regulations applicable in the United States, or other patient privacy regulations that may be applicable in other jurisdictions. In this regard, a "face" is not identified in the operation 36 in the case of a frame that only depicts the glottis of the patient (as when the distal end of the laryngoscope blade is engaged to perform the intubation), and is preferably also not identified in the case of a frame that only depicts the open mouth of the patient. These features are not sufficient to be "identifying" in most cases, and images of the open mouth prior to engagement of the laryngoscope may be needed to demonstrate the state of the patient's dental and/or oral features prior to commencement of the tracheal intubation procedure.

The server computer 34 is further programmed to perform an operation 38 in which the anonymized video is tagged with a video recording timestamp (for example, the video may be assigned a timestamp indicating when the video began to be recorded, and optionally also a time when the video recording stopped) and at least one of (i) a surgical location, and/or (ii) an anesthesiologist identifier. The surgical location may be variously specified. For example, the video monitor 15 may have a serial number and that serial number serves as the surgical location (insofar as the video monitor is owned by a single hospital at the time of the surgical procedure). In another approach, if the video monitor 15 has GPS capability then the surgical location may be specified by the GPS coordinates of the video monitor 15 acquired at the time of the video recording. The anesthesiologist identifier may be provided if, for example, the anesthesiologist is required to enter his or her name or employee number or other anesthesiologist identifier into the video monitor 15 when using it.

The server computer 34 is further programmed to store the anonymized video with the tags on a non-transitory storage medium 40 (e.g., a hard disk drive or other magnetic storage medium, or an optical disk or other optical storage medium, or a solid state drive or other electronic storage medium, or so forth). It should be noted that the server computer 34 may be a single computer, or may be a plurality of interconnected computers, e.g. a cluster of server computers or an ad hoc combination of server computers forming a cloud-based computing resource.

While the foregoing describes the processing and storage of anonymized video of a single tracheal intubation procedure, it will be appreciated that this process is repeated for each tracheal intubation procedure, and may optionally also be performed for a plurality of video laryngoscopes. Hence, the storage medium 40 may in general store a large number of tracheal intubation videos performed with a number of different video laryngoscopes by a number of different anesthesiologists. In most cases, the stored video is never retrieved.

If, however, a question arises as to a particular tracheal intubation procedure (for example, because a malpractice claim has been alleged respecting that particular tracheal intubation procedure), then the anonymized video for that particular tracheal intubation procedure can be retrieved at a workstation computer 42 running a suitable retrieval user interface (UI) on the basis of the tagged timestamp and location and/or anesthesiologist. The retrieved video can then serve as video evidence for defending against the malpractice claim.

It should be noted that the system of FIG. 3 which leverages a video laryngoscope to provide an auditable record of tracheal intubation procedures can be used with any type of video laryngoscope that has Internet or network connectivity, or that is paired with a video monitor having Internet or network connectivity. Hence, it is not limited to video laryngoscopes of the designs of FIGS. 1 and 2.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A video laryngoscope comprising:
a handle;
a laryngoscope blade having a proximal end connected with the handle and a distal end that is distal from the handle;
a chemiluminescent light source disposed inside the handle;
one or more photovoltaic cells disposed inside the handle and optically coupled with the chemiluminescent light source to convert chemiluminescence emitted by the chemiluminescent light source into electrical power; and
an image sensor disposed on the laryngoscope blade or in the handle and configured to image the glottis of an associated patient when the distal end of the laryngoscope blade operatively engages the tongue of the associated patient;
wherein the image sensor is powered by the electrical power produced by the one or more photovoltaic cells.

2. The video laryngoscope of claim 1 further comprising:
a wireless transmitter disposed in the laryngoscope blade or in the handle and operatively connected with the image sensor to wirelessly transmit images acquired by the image sensor to an associated video monitor;
wherein the wireless transmitter is powered by the electrical power produced by the one or more photovoltaic cells.

3. The video laryngoscope of claim 1 wherein the image sensor is disposed in the handle or in the proximal end of the laryngoscope blade, and the laryngoscope further comprises:
an image conduit having a first end disposed on the laryngoscope to view the glottis of the associated patient when the distal end of the laryngoscope blade operatively engages the tongue of the associated patient, the image conduit extending along at least a portion of the laryngoscope blade and terminating at a second end that is operatively connected with the image sensor.

4. The video laryngoscope of claim 1 further comprising:
a light emitting diode (LED) disposed on the laryngoscope blade or in the handle and configured to illuminate the glottis of the associated patient when the laryngoscope blade operatively engages the tongue of the associated patient;
wherein the LED is powered by the electrical power produced by the one or more photovoltaic cells.

5. The video laryngoscope of claim 4 wherein the LED is disposed in the handle or in the proximal end of the laryngoscope blade, and the laryngoscope further comprises:
a light conduit optically coupled with the LED and extending along a portion of the laryngoscope blade.

6. The video laryngoscope of claim 5 further comprising:
at least one optical component optically coupled with or integrally formed into an end of the light conduit distal from the LED to form light emitted by the LED and conducted by the light conduit into illumination for illuminating the glottis of the associated patient when the laryngoscope blade operatively engages the tongue of the associated patient.

7. The video laryngoscope of claim 4 wherein:
an optical output power of the LED is not effective to provide illumination for visual observation of the glottis of the associated patient when the laryngoscope blade operatively engages the tongue of the associated patient; and
the optical output power of the LED is effective to provide illumination for imaging of the glottis of the associated patient via the image sensor when the laryngoscope blade operatively engages the tongue of the associated patient.

8. The video laryngoscope of claim 4 wherein the LED illuminates the glottis with both visible light and ultraviolet light.

9. The video laryngoscope of claim 8 wherein:
an optical output power of the chemiluminescent light source is not effective to provide illumination via the light conduit for visual observation of the glottis of the associated patient when the laryngoscope blade operatively engages the tongue of the associated patient; and
the optical output power of the chemiluminescent light source is effective to provide illumination via the light conduit for imaging of the glottis of the associated patient via the image sensor when the laryngoscope blade operatively engages the tongue of the associated patient.

10. The video laryngoscope of claim 1 further comprising:
a light conduit optically coupled with the chemiluminescent light source and extending along a portion of the laryngoscope blade.

11. The video laryngoscope of claim 10 further comprising:
at least one optical component optically coupled with or integrally formed into an end of the light conduit distal from the chemiluminescent light source to form chemiluminescence emitted by the chemiluminescent light source and conducted by the light conduit into illumination for illuminating the glottis of the associated patient when the laryngoscope blade operatively engages the tongue of the associated patient.

12. The video laryngoscope of claim 10 wherein a portion of the light conduit extends into the handle and the chemiluminescent light source is embedded in the portion of the light conduit extending into the handle.

13. The video laryngoscope of claim 1 wherein the chemiluminescent light source disposed inside the handle includes:
- a first container containing a first reactant fluid; and
- a second container disposed inside the first container and containing second reactant fluid separated from the first reactant fluid by the second container;
- wherein the first reactant fluid and the second reactant fluid when combined react to generate the chemiluminescence.

14. The video laryngoscope of claim 13 wherein:
- one of the first reactant fluid or the second reactant fluid comprises hydrogen peroxide; and
- at least one of the first reactant fluid or the second reactant fluid comprises one or more fluorophores;
- the first container optionally further including at least one additional fluorophore disposed on an inner wall of the first container.

15. The video laryngoscope of claim 13 further comprising:
- an activation mechanism configured to rupture the second container whereby the second reactant fluid combines and reacts with the first reactant fluid to generate the chemiluminescence.

16. The video laryngoscope of claim 15 wherein the activation mechanism is one of:
- a plunger mounted on the handle and arranged to rupture the second container;
- a deformable portion of the handle arranged to rupture the second container when deformed by an external force;
- a weight disposed inside the first container and arranged to rupture the second container in response to shaking of the handle; or
- said second container disposed movably inside the first container whereby the second container ruptures in response to shaking of the handle.

17. A laryngoscope comprising:
- a handle;
- a laryngoscope blade having a proximal end connected with the handle and a distal end that is distal from the handle;
- an electrical coil disposed inside the handle and configured to emit electrical power comprising an electrical current induced in the electrical coil; and
- at least one of a light emitting diode (LED) and/or an image sensor disposed on or in the laryngoscope and arranged to illuminate and/or view the glottis of an associated patient when the laryngoscope blade operatively engages the tongue of the associated patient, the LED and/or image sensor being powered by the electrical power emitted by the electrical coil.

18. The laryngoscope of claim 17 wherein no battery is disposed in the handle.

19. The laryngoscope of claim 17 further comprising:
- a radio frequency (RF) power generator separate from the handle and separate from the laryngoscope blade, the RF power generator generating RF power inductively coupling with the electrical coil disposed in the handle to induce the electrical current in the electrical coil disposed in the handle.

20. A system for recording tracheal intubation procedures performed by a plurality of video laryngoscopes, the system comprising:
- a server computer configured to connect with a video laryngoscope of the plurality of video laryngoscopes and to receive video from the connected video laryngoscope and to process the video by operations including performing face identification on the video and removing any frames of the video depicting a human face to generate anonymized video, tagging the anonymized video with a video recording timestamp and at least one of (i) a surgical location and/or (ii) or an anesthesiologist identifier, and storing the anonymized video with the tags on a non-transitory storage medium; and
- at least one user interface device configured to retrieve selected anonymized video from the non-transitory storage medium wherein the selected anonymized video is selected on the basis of the video recording timestamp and the surgical location and/or anesthesiologist identifier.

* * * * *